United States Patent
Baum

(10) Patent No.: US 12,201,114 B2
(45) Date of Patent: Jan. 21, 2025

(54) AQUEOUS 1,2-BENZISOTHIAZOLINE-3-ONE DISPERSIONS

(71) Applicant: Thor GmbH, Speyer (DE)

(72) Inventor: Rüdiger Baum, Neulussheim (DE)

(73) Assignee: Thor GmbH, Speyer (DE)

( * ) Notice: Subject to any disclaimer, the term of this patent is extended or adjusted under 35 U.S.C. 154(b) by 590 days.

(21) Appl. No.: 17/439,455

(22) PCT Filed: Feb. 14, 2020

(86) PCT No.: PCT/EP2020/000042
§ 371 (c)(1),
(2) Date: Sep. 15, 2021

(87) PCT Pub. No.: WO2020/187440
PCT Pub. Date: Sep. 24, 2020

(65) Prior Publication Data
US 2022/0151233 A1 May 19, 2022

(30) Foreign Application Priority Data
Mar. 19, 2019 (EP) .................... 19000134

(51) Int. Cl.
*A01N 43/80* (2006.01)
*C07D 275/06* (2006.01)

(52) U.S. Cl.
CPC .......... *A01N 43/80* (2013.01); *C07D 275/06* (2013.01)

(58) Field of Classification Search
CPC ....... A01N 43/80; A01N 25/04; C07D 275/06
See application file for complete search history.

(56) References Cited

U.S. PATENT DOCUMENTS 4,188,376 A  2/1980 Brand et al.

FOREIGN PATENT DOCUMENTS

| WO | WO 9416564 A1 | 8/1994 | |
|---|---|---|---|
| WO | WO-2008104310 A2 * | 9/2008 | ............. A01N 43/80 |
| WO | WO 2012158425 A1 | 11/2012 | |
| WO | PCT/EP2020/000042 | 2/2020 | |

OTHER PUBLICATIONS

PCT International Search Report and Written Opinion for PCT/EP2020/000042 dated Jul. 28, 2020.

* cited by examiner

*Primary Examiner* — Zohreh A Fay
(74) *Attorney, Agent, or Firm* — McCarter & English, LLP

(57) ABSTRACT

The invention relates to aqueous benzisothiazoline-3-one dispersions of sodium-1,2-benzisothiazoline-3-one particles dispersed in water. The dispersions contain: (a) between 15 wt.-% and 35 wt.-% of sodium-1,2-benzisothiazoline-3-one; and (b) ad. 100 wt.-% of water having a content of sodium ion in the range from 4 wt.-% to 10 wt.-% with respect to water contained in the dispersion. The invention further relates to the use of the claimed dispersions for preserving water-based products of all types, in particular, cleaning and household products, plastics dispersions, paints, plasters, adhesives, sealing compounds, paper coating materials, textile softeners and sizing agents, washing raw materials, surfactants, polishing agents, spinning baths, cooling lubricants, leather treatment agents and silicone and bitumen emulsions.

13 Claims, No Drawings

AQUEOUS 1,2-BENZISOTHIAZOLINE-3-ONE DISPERSIONS

CROSS-REFERENCE TO RELATED APPLICATIONS

This application is a 35 U.S.C. § 371 National Stage filing of International Application No. PCT/EP2020/000042, filed on Feb. 14, 2020, which claims priority to European Patent Application 19000134.7, filed on Mar. 19, 2019.

The invention relates to aqueous benzisothiazoline-3-one dispersions of sodium-1,2-benzisothiazoline-3-one particles dispersed in water. The dispersions contain: (a) between 15 wt.-% and 35 wt.-% of sodium-1,2-benzisothiazoline-3-one; and (b) ad. 100 wt.-% of water having a content of sodium ion in the range from 4 wt.-% to 10 wt.-% with respect to water contained in the dispersion. The invention further relates to the use of the claimed dispersions for preserving water-based products of all types, in particular, cleaning and household products, plastics dispersions, paints, plasters, adhesives, sealing compounds, paper coating materials, textile softeners and sizing agents, washing raw materials, surfactants, polishing agents, spinning baths, cooling lubricants, leather treatment agents and silicone and bitumen emulsions.

The 1,2-benzisothiazoline-3-one (BIT) or its sodium, potassium and lithium salts is an active ingredient that has long been used in practice to produce formulations with microbicidal effect. The active ingredient is characterized by good chemical and thermal stability, and basically has broad antimicrobial activity against bacteria, fungi, and yeasts.

In order to make this active ingredient available in a form that is easy to handle and dose, aqueous solutions of the alkali metal salts of BIT or aqueous dispersions in which the BIT is dispersed in particulate form in the water phase are usually prepared from crude BIT obtained during synthesis. Aqueous solutions are however limited to BIT contents of less than 10 wt.-% BIT. Higher concentrated solutions tend to crystallize at temperatures below 20° C. and are therefore not sufficiently stable for storage.

According to the teaching of DE 28 40 273 A1, organic solvents containing certain hydroxyl groups, such as propylene glycol, are added to the BIT in the form of its alkali metal salt dissolved in water in order to produce allegedly stable aqueous BIT solutions in concentrations higher than 10%. However, the addition of such solvents makes the solutions more expensive and is also undesirable from an ecological point of view.

Furthermore, U.S. Pat. No. 4,871,754, discloses aqueous formulations of the lithium salt of 1,2-benzisothiazoline-3-one. However, these preparations do not offer sufficiently low temperature stability at higher BIT concentrations, and also require the addition of a water-miscible organic solvent, such as 1,2-propylene glycol, which is associated with the aforementioned disadvantages.

Therefore, it is advantageous to make use of aqueous solutions of 1,2-benzisothiazoline-3-one which are as highly concentrated as possible, are free of glycol-based solvents, and dissolve rapidly during use.

PCT Disclosure WO 2012/158425 A1 discloses highly concentrated aqueous solutions of 1,2-benzisothiazoline-3-one containing about 0.1 to about 30 wt.-% 1,2-benzisothiazoline-3-one, about 5 to 15 wt.-% alkali metal salt, about 50 to about 85 wt.-% water, and about 0.1 to about 5 wt.-% chelating agents. In readjusting the compositions according to this publication, it has been found, however, that they are not sufficiently stable during storage, in particular, at temperatures below 20° C.

Furthermore, aqueous dispersions of 1,2-benzisothiazoline-3-one with a content in the range from about 20 wt.-% are commercially available. In use, these compositions do however dissolve comparatively slowly in the product to be preserved, which in certain applications results in these particles being filtered off and thus no longer being available as an active ingredient. Dispersions of the alkali metal salts of BIT are not commercially available, as they tend to form larger particles or crystals and no homogeneous, storable product is obtained.

Based on the prior art, it is the task of the invention to provide more stable, 1,2-benzisothiazoline-3-one dispersions with the highest possible content of 1,2-benzisothiazoline-3-one when compared to known prior art compositions. A further task of the invention is to provide stable 1,2-benzisothiazoline-3-one dispersions which are as concentrated as possible and which, when used as a biocide, dissolve more rapidly in the product to be preserved compared to known prior art dispersions.

This task is solved by an aqueous benzisothiazoline-3-one dispersion of sodium-1,2-benzisothiazoline-3-one particles dispersed in water, containing:
(a) 15 wt.-% to 35 wt.-%, preferably 20 wt.-% to 30 wt.-% sodium-1,2-benzisothiazoline-3-one and
(b) ad. 100 wt.-% water, with a sodium ion content in the range from 4 to 10 wt.-%, with respect to the water contained in the dispersion.

Surprisingly, the present invention provides new aqueous dispersions which are more stable in storage than the known prior art 1,2-benzisothiazoline-3-one dispersions (BIT dispersions) and which new aqueous dispersions advantageously overcome the previously described disadvantages of the prior art. In this context, stability in storage means that the dispersions according to the invention exhibit virtually no particle growth or crystal growth, even when stored for longer periods. In particular, within the scope of this invention, aqueous BIT dispersions are provided which, compared to known prior art dispersions, dissolve much more rapidly in the water phase of the products to be preserved when used as a biocide.

The BIT dispersion according to the invention is characterized by the fact that it contains particles of sodium-1,2-benzisothiazoline-3-one (Na-BIT) dispersed in a water phase. The Na-BIT particles have a median particle size (d50) of less than 200 μm. Preferably, the Na-BIT particles dispersed in the water phase have a median particle size (d50) in the range from 10 to 40 μm.

The aforementioned particles of the sodium salt of 1,2-benzisothiazoline-3-one substantially consist of the sodium salt of 1,2-benzisothiazoline-3-one, such that in addition to the sodium salt of 1,2-benzisothiazoline-3-one, other BIT salts may be present in the particles in small amounts.

As component (a), the BIT dispersion according to the invention contains 15 wt.-% to 35 wt.-%, preferably 20 wt.-% to 30 wt.-%, particularly preferably 22 wt.-% to 29 wt.-% of sodium 1,2-benzisothiazoline-3-one, in each case with respect to the total weight of the BIT dispersion according to the invention.

As component (b), the BIT dispersion according to the invention contains ad. 100 wt.-% water, with a content of sodium ions in the range from 4 wt.-% to 10 wt.-%, preferably 5 wt.-% to 9 wt.-%, particularly preferably 6 wt.-% to 8 wt.-%, in each case with respect to the water contained in the dispersion, or the water phase of the dispersion. "Content of sodium ions" means, in the context of the invention, the quantity of sodium ions that can be detected as dissolved sodium ions in the water phase of the dispersion according to the invention. The sodium ions of the sodium salt of the 1,2-benzisothiazoline-3-one that are not dissolved in the water phase are not taken into account.

The content of sodium ions in the water phase of the dispersion within the limits given above can be adjusted by adding a salt containing sodium ions, and also by using an excess of sodium hydroxide solution in the neutralization of the BIT. In principle, all sodium ion-containing salts or mixtures that have sufficient solubility at the desired storage temperatures of the dispersion according to the invention and which do not react with the sodium salt of the benzisothiazoline-one can be used as the source of the sodium ions. Preferably, the salts are selected from the group consisting of sodium chloride, sodium nitrate, sodium carbonate, sodium acetate, sodium citrate, sodium lactate and sodium formate, or mixtures thereof. According to a particularly preferred embodiment of the invention, the sodium ion-containing salt used is sodium chloride. According to an alternatively preferred embodiment of the invention, the dispersions according to the invention also contain, in addition to the sodium ion-containing salts mentioned above, sodium salts of active ingredients having a biocidal effect, such as sodium salicylate, sodium benzoate and sodium pyrithione, or mixtures thereof. The counterions of the sodium ion-containing salts, such as the chloride ions, will also be referred to below as the counterions of the sodium ion source.

The content of sodium ions in the water phase of the dispersions advantageously causes the particles of the sodium salt of 1,2-benzisothiazoline-3-one obtained in the dispersion according to the invention to remain in the dispersed state as such, and interact only to a limited extent with the water phase. This advantageously ensures that the median particle size of the sodium 1,2-benzisothiazoline-3-one particles remains virtually constant during storage of the dispersion and that growth of the particles is at least largely avoided.

The content of water, relative to the total weight of the BIT dispersion according to the invention, is generally in the range from 40 wt.-% to 80 wt.-%, preferably in the range from 50 wt.-% to 75 wt.-%, particularly preferably in the range from 60 wt.-% to 70 wt.-%, in each case relative to the total weight of the BIT dispersion according to the invention.

According to a preferred embodiment of the invention, the aqueous dispersions contain, in addition to components (a) and (b), at least 0.1 wt.-% to 1.0 wt.-%, preferably 0.2 wt.-% to 0.4 wt.-% of one thickening agent as a further component (c), in each case with respect to the total weight of the BIT dispersion according to the invention. The presence of component (c), the thickening agent, provides additional stabilization of the dispersions according to the invention and avoids sedimentation.

The thickening agent is preferably selected from the group consisting of xanthan gum, carrageenan, alginates, tyloses, carboxymethyl cellulose, microcrystalline cellulose, hydroxyethyl cellulose and/or polyacrylates. According to a particularly preferred embodiment of the invention, the thickening agent present as component (c) is xanthan gum.

According to the invention, the biocide composition is characterized in that it has a pH in the range from pH 8 to pH 12, preferably in the range from pH 8.0 to pH 10.

According to a preferred embodiment of the invention, the dispersion according to the invention is substantially free of volatile organic compounds (VOC), glycols, derivatives of glycols, such as 1,2-propanediol, glycerol and/or derivatives of glycerol. "Substantially free" in this context means that the dispersion contains 0 wt.-% to 5 wt.-%, preferably 0 wt.-% to 2 wt.-%, particularly preferably 0 wt.-% to 0.5 wt.-% of volatile organic compounds (VOCs), glycols, derivatives of glycols, glycerol and/or derivatives of glycerol. According to a particularly preferred embodiment of the invention, the dispersion according to the invention is free of volatile organic compounds (VOC), glycols, derivatives of glycols, glycerol and/or derivatives of glycerol.

If necessary, the dispersions according to the invention contain, in addition to components (a), (b) and optionally component (c), further components such as defoaming agents, wetting agents, dispersing agents and protective colloids. These are known to the person skilled in the art and are contained as required in the dispersion in appropriate amounts.

A dispersion containing exclusively components (a), (b), the counterions of the sodium ion source, preferably the chloride ions, and optionally component (c) in the stated weight ratios, without the presence of any further active component with microbicidal effect, is referred to in the context of this invention as a "dispersion according to the invention". The "dispersion according to the invention" may comprise, in addition to components (a), (b), the counterions of the sodium ion source and, optionally, component (c) in the indicated weight ratios, one or more further components. The further component or components may have a microbicidal effect, or they may have no microbicidal effect, for example they may be a solvent, dispersant or suspending agent.

In a further embodiment, the "dispersion according to the invention" comprises components (a), (b), the counterions of the sodium ion source and optionally component (c) in the proportions indicated above (i.e. the dispersion according to the invention). This means that the dispersion according to the invention contains only components (a), (b), the counterions of the sodium ion source and optionally component (c).

In a further embodiment of the invention, the dispersion according to the invention consists "essentially" of the components (a), (b) according to the invention, the counterions of the sodium ion source and, optionally, component (c), i.e., in addition to these, one or also several other components may well be present, but these are present only in a very small quantity.

The invention further relates to the use of the dispersions defined above for the preservation of technical products containing water or that can be diluted by water, against attack and/or destruction by microorganisms. Preferably, the dispersions according to the invention can be used to preserve functional liquids and water-containing technical products that are susceptible to microbial attack. In the context of use, the dispersion according to the invention is characterized in that, in the context of intended use, it dissolves significantly faster, when compared to commercially available dispersions, in the water phase of the technical products to be preserved containing water or that can be diluted by water.

The use of the dispersions according to the invention is particularly suitable, due to the broad spectrum of action of the BIT, for the preservation of cleaning and household products, plastic dispersions, paints, plasters, adhesives, sealing compounds, paper coating compounds, textile softeners and sizing agents, washing raw materials, surfactants, polishing agents, spinning baths, cooling lubricants, leather treatment agents and silicone and bitumen emulsions. Particularly preferably, the dispersions according to the invention are suitable for the preservation of cleaning and household products, as well as plastics dispersions and paints.

The application concentrations of the dispersions to be used according to the invention depend on the type and occurrence of the microorganisms to be controlled, the initial microbial load and the composition of the technical product or material to be protected. The optimum application quantity for a particular application can be determined by laboratory tests prior to practical use. Generally, the application concentrations are in the range from 0.01 wt.-% to 5 wt.-%, preferably from 0.02 wt.-% to 0.5 wt.-% of the dispersion according to the invention, relative to the technical product, or material, to be protected.

According to one embodiment, the invention therefore also relates to a water-containing technical product selected from cleaning and household products, plastics dispersions, paints, plasters, adhesives, sealing compounds, paper coating compounds, textile softening and sizing agents, washing raw materials, surfactants, polishing agents, spinning baths, cooling lubricants, leather treatment agents and silicone and bitumen emulsions, which contains the dispersion according to the invention, preferably in an amount in the range from 0.01 wt.-% to 5 wt.-%, preferably from 0.02 wt.-% to 0.5 wt.-%, with respect to the technical product to be protected.

The invention further relates to a method for controlling the growth of at least one microorganism in an aqueous liquid, comprising the step of adding an aqueous benzisothiazoline-3-one dispersion of sodium 1,2-benzisothiazoline-3-one particles dispersed in water, comprising:

(a) between 15 wt.-% and 35 wt.-% of sodium-1,2-benzisothiazoline-3-one; and (b) ad. 100 wt.-% water, with a content of sodium ions in the range from 4 wt.-% to 10 wt.-%, with respect to the water contained in the dispersion, to an aqueous liquid, such that the growth of the at least one microorganism in the liquid is inhibited, or at least suppressed. According to one embodiment of the invention, the aqueous liquid is a detergent or cleaning agent, or a polymer dispersion, or a dispersion paint.

In the framework of use of the dispersion according to the invention in carrying out the above-described process for preserving aqueous products or for controlling the growth of at least one microorganism in an aqueous liquid, it has been found that the dispersion according to the invention dissolves significantly faster in the water phase of the aqueous liquid to be preserved compared to commercially available dispersions. This makes it possible, for example, to achieve considerably shorter incorporation times or stirring times. A further advantage in the use of the dispersions according to the invention for the preservation of polymer dispersions or dispersion paints is that, due to the improved solubility of the dispersion according to the invention in the water phase of these products, the sodium-1,2-benzisothiazoline-3-one particles contained are bound to a significantly lesser extent in the polymer matrix of the polymer dispersions or dispersion paints, and can therefore also only react to a lesser extent with any polymerization catalysts still present in the matrix.

The dispersions according to the invention can be prepared, for example, by preloading water and sodium hydroxide and adding the 1,2-benzisothiazoline-3-one, preferably in the form of a moist filter cake, to water while stirring at a temperature of about 40 to 60° C. and stirring the resulting mixture at a temperature of about 40 to 60° C., until the solid has dissolved. The appropriate amount of sodium chloride is added thereafter and the composition is cooled to room temperature. Formulation vehicles, depending on the type, are introduced together with the water, or added at the end. In a next process step, the precipitated sodium-1,2-benzisothiazoline-3-one particles are ground to the desired particle size, preferably to a Hegman gage particle size of <60 µm.

According to an alternative preparation procedure, a BIT Na solution nearing saturation at 50° C. was initially prepared and this solution, with vigorous stirring on the dissolver, was stirred into a receiver of water, protective colloid, and sodium chloride. The resulting BIT Na dispersion was stabilized with xanthan gum and a Hegman gage particle size of less than 200 µm.

According to a preferred embodiment of the invention, the dispersion according to the invention contains the following components, or consists of the following components:

Composition 1:

| 1,2-Benzisothiazoline-3-one, sodium salt | 23 wt.-%. |
|---|---|
| NaCl | 12 wt.-% |
| Water | 64.7 wt.-% |
| Xanthan gum | 0.3 wt.-% |

Composition 2:

| 1,2-Benzisothiazoline-3-one, sodium salt | 29 wt.-% |
|---|---|
| NaCl | 10 wt.-% |
| Water | 60.7 wt.-% |
| Xanthan gum | 0.3 wt.-% |

The following examples and comparative examples are provided to further illustrate this invention.

To investigate the stability of the dispersions according to the invention, the dispersions defined in Table 1 shown below were prepared. The median particle size of the sodium-1,2-benzisothiazoline-3-one particles was in the range of 10 to 40 µm. Dispersions 1, 2, 3, 5 and 6 are dispersions according to the invention, and dispersions 4C and 7C are used for comparison.

To investigate the storage stability of the respective dispersions, the dispersions underwent 5 cycles in which they were stored at 40° C. for 16 hours each and then allowed to cool at 20° C. for 8 hours each.

As can be seen from the results presented in Table 1, no growth of the sodium-1,2-benzisothiazoline-3-one particles could be observed in Examples 1, 2, 3, 5, and 6, whereas pronounced crystal formation was observed in comparative examples 4C and 7C.

TABLE 1

Examples 1, 2, 3, 5 and 6 and comparative examples 4C and 7C

| Components | 1 Wt.-% | 2 Wt.-% | 3 Wt.-% | 4C Wt.-% | 5 Wt.-% | 6 Wt.-% | 7C Wt.-% |
|---|---|---|---|---|---|---|---|
| BIT nominal | 20 | 25 | 20 | 20 | 15 | 30 | 20 |
| BIT 85% strength | 23.5 | 29.4 | 23.5 | 23.5 | 17.7 | 35.3 | 23.5 |
| NaOH for NaBIT | 5.3 | 6.6 | 5.3 | 5.3 | 4 | 8 | 5.3 |
| NaOH excess | 0 | 1 | 0 | 0 | 0 | 0 | 0 |
| NaCl | 15 | 12.5 | 10 | 5 | 15 | 15 | 0 |
| Xanthan gum | 0.3 | 0.25 | 0.3 | 0.3 | 0.3 | 0.2 | 0.3 |
| Water | 55.9 | 50.25 | 60.9 | 65.9 | 63 | 41.5 | 70.9 |
| Water content (total) | 61.8 | 57.6 | 66.8 | 71.8 | 67.4 | 50.4 | 76.8 |
| Dissolved Na$^+$/in % per water phase* | 7.7 | 7.7 | 5.1 | 2.6 | 7.2 | 9.0 | 0.0 |
| NaCl in the water phase | 19.5 | 17.6 | 13.0 | 6.5 | 18.2 | 22.9 | 0.0 |
| Stability after five cycles of heating to 40° C. and cooling to 20° C. | OK | OK | OK | crystal formation | OK | OK | distinct crystal formation |

*Water phase = water plus NaCl plus NaOH excess

The invention claimed is:

1. Aqueous benzisothiazoline-3-one dispersion of sodium-1,2-benzisothiazoline-3-one particles dispersed in water, comprising:
   (a) between 15 wt.-% and 35 wt.-% of sodium-1,2-benzisothiazoline-3-one; and
   (b) up to 100 wt.-% of water having a content of sodium ion in the range from 4 wt.-% to 10 wt.-%, with respect to water contained in the dispersion.

2. A dispersion according to claim 1, comprising as further component:
   (c) 0.1 wt.-% to 1 wt.-% of at least one thickening agent.

3. A dispersion according to claim 2, characterized in that the thickening agent is selected from the group consisting of xanthan gum, carrageenan, alginates, tyloses, carboxymethyl cellulose, microcrystalline cellulose, hydroxyethyl cellulose and polyacrylates.

4. A dispersion according to claim 1, characterized in that the dispersion contains the sodium-1,2-benzisothiazoline-3-one in the form of particles having a median particle size in the range from 10 to 40 μm.

5. A dispersion according to claim 1, wherein the dispersion contains, as component (a), between 20 wt.-% and 30 wt.-% of sodium-1,2-benzisothiazoline-3-one.

6. A dispersion according to claim 1, characterized in that the dispersion has a pH in the range from pH 8 to pH 12.

7. A dispersion according to claim 1, characterized in that the dispersion contains 0 wt % to 5 wt % of volatile organic compounds (VOC), glycols, and/or glycerol.

8. A method of applying the Use of a dispersion according to claim 1 as a preservative for protecting water-containing products from attack and/or destruction by microorganisms.

9. The method according to claim 8, characterized in that the water-containing product is selected from the group consisting of cleaning and household products, plastic dispersions, paints, plasters, adhesives, sealing compounds, paper coating compounds, textile softening and sizing agents, washing raw materials, surfactants, polishing agents, spinning baths, cooling lubricants, leather treatment agents, silicone emulsions and bitumen emulsions.

10. A water-containing product selected from the group consisting of cleaning and household products, plastics dispersions, paints, plasters, adhesives, sealants, paper coating compounds, textile softeners and sizing agents, washing raw materials, surfactants, polishing agents, spinning baths, cooling lubricants, leather treatment agents, silicone emulsions, and bitumen emulsions, comprising a dispersion according to claim 1.

11. An aqueous product according to claim 10, comprising a dispersion according to claim 1 in an amount of 0.01 wt.-% to 5 wt.-%.

12. A method for controlling the growth of at least one microorganism in an aqueous liquid comprising the step of adding an aqueous benzisothiazoline-3-one dispersion of water dispersed sodium-1,2-benzisothiazoline-3-one particles containing:
   (a) between 15 wt.-% and 35 wt.-% of sodium-1,2-benzisothiazoline-3-one; and
   (b) up to 100 wt.-% of water having a content of sodium ions in the range from 4 wt.-% to 10 wt.-%, with respect to the water contained in the aqueous benzisothiazoline-3-one dispersion, to an aqueous liquid, so that the growth of the at least one microorganism in the liquid is inhibited, or at least suppressed.

13. The method according to claim 12, characterized in that the aqueous liquid is a detergent or cleaning agent or a polymer dispersion or an emulsion paint.

* * * * *